US011983824B2

(12) United States Patent
Avisar et al.

(10) Patent No.: US 11,983,824 B2
(45) Date of Patent: May 14, 2024

(54) SYSTEM AND METHOD FOR AUGMENTING AND SYNCHRONIZING A VIRTUAL MODEL WITH A PHYSICAL MODEL

(71) Applicant: Surgical Theater, Inc., Mayfield Village, OH (US)

(72) Inventors: Mordechai Avisar, Highland Heights, OH (US); Alon Yakob Geri, Orange Village, OH (US)

(73) Assignee: SURGICAL THEATER, INC., Beachwood, OH (US)

( * ) Notice: Subject to any disclaimer, the term of this patent is extended or adjusted under 35 U.S.C. 154(b) by 208 days.

(21) Appl. No.: 17/163,471

(22) Filed: Jan. 31, 2021

(65) Prior Publication Data
US 2021/0241534 A1    Aug. 5, 2021

Related U.S. Application Data

(60) Provisional application No. 63/062,921, filed on Aug. 7, 2020, provisional application No. 62/968,340, filed on Jan. 31, 2020.

(51) Int. Cl.
*G06T 19/00* (2011.01)
*G06F 3/01* (2006.01)
(Continued)

(52) U.S. Cl.
CPC ............ *G06T 19/006* (2013.01); *G06F 3/012* (2013.01); *G06F 16/245* (2019.01); *G06T 7/246* (2017.01);
(Continued)

(58) Field of Classification Search
None
See application file for complete search history.

(56) References Cited

U.S. PATENT DOCUMENTS 9,767,608 B2 *   9/2017  Lee ................... G06T 19/006
2017/0367771 A1 * 12/2017 Tako .................. G06T 19/003
(Continued)

FOREIGN PATENT DOCUMENTS

JP          2018097645 A  *  6/2018
WO   WO-2017138153 A1  *  8/2017  ............. G06F 13/00

*Primary Examiner* — Steven Z Elbinger

(57) ABSTRACT

A method includes: receiving synchronization and navigation data from a navigation system; generating a physical frame of reference with respect to a registered physical model based on the synchronization and navigation data; registering an augmented reality head mounted display with the navigation system using the synchronization and navigation data; receiving data representative of a virtual model; anchoring the virtual model to the physical frame of reference; receiving tracking data indicative of the position and angle of view of the augmented reality head mounted display with respect to the physical frame of reference; and responsive to determining that the physical model is within a field of view of the augmented reality head mounted display: rendering a virtual image from the virtual model in real time based on the received tracking data; and streaming the virtual image to the augmented reality head mounted display, thereby generating a synchronized and augmented realty view.

17 Claims, 7 Drawing Sheets

(51) Int. Cl.
*G06F 16/245* (2019.01)
*G06T 7/246* (2017.01)
*G06T 7/33* (2017.01)
*G06T 19/20* (2011.01)
*G16H 30/20* (2018.01)

(52) U.S. Cl.
CPC .............. *G06T 7/33* (2017.01); *G06T 19/003* (2013.01); *G06T 19/20* (2013.01); *G16H 30/20* (2018.01); *G06T 2207/30204* (2013.01); *G06T 2210/41* (2013.01); *G06T 2219/2004* (2013.01)

(56) References Cited

U.S. PATENT DOCUMENTS

| | | | |
|---|---|---|---|
| 2020/0246074 A1* | 8/2020 | Lang | A61F 2/3859 |
| 2021/0059755 A1* | 3/2021 | Villain | G16H 50/50 |
| 2021/0074183 A1* | 3/2021 | Van Flute | A61B 34/10 |
| 2021/0093415 A1* | 4/2021 | Moore | A61B 90/08 |

\* cited by examiner

SYSTEM AND METHOD FOR AUGMENTING AND SYNCHRONIZING A VIRTUAL MODEL WITH A PHYSICAL MODEL

CROSS-REFERENCE TO RELATED APPLICATION

This application claims priority from U.S. provisional patent application Ser. No. 62/968,340 filed on Jan. 31, 2020 and from U.S. provisional patent application Ser. No. 63/062,921 filed on Aug. 7, 2020, both of which are incorporated by reference herein in their entirety.

FIELD OF DISCLOSURE

The present disclosure relates to the field of surgical procedures and more specifically to the field of augmented reality surgical procedures.

BACKGROUND

Surgical procedures may often be complex and time sensitive and vary in scope from one patient to another. For example, in the case of an aneurysm repair, the point of repair may vary in terms or procedural requirements depending on the exact location, size, and so on. Therefore, the efficiency of the procedure is highly critical and detailed planning based on the patient specific local geometry and physical properties of the area on which surgery is being performed is fundamental. To achieve a new level of pre-surgery preparation, 3-dimensional renderings based on CT and MRI images are being increasingly utilized. However, those renderings offer only minor benefits, standing alone, for surgery rehearsal. Moreover, existing techniques for studying a patient's specific anatomy prior to or during surgery may be invasive to the patient and may also distract a surgeon or require the surgeon to temporarily move his attention away from a region where a surgical procedure is being performed.

SUMMARY

An example method for synchronizing and augmenting a virtual model with a physical model, includes the steps of: an AR synchronization computer receiving synchronization and navigation data from a navigation system and generating a physical frame of reference with respect to a registered physical model based on the synchronization and navigation data; the AR synchronization computer registering an augmented reality head mounted display with the navigation system using the synchronization and navigation data, thereby enabling tracking movement of the augmented reality head mounted display with respect to the physical model; the AR synchronization computer receiving data representative of a virtual model from a virtual model database; the AR synchronization computer anchoring the virtual model to the physical frame of reference; the AR synchronization computer receiving tracking data indicative of the position and angle of view of the augmented reality head mounted display with respect to the physical frame of reference; and responsive to the AR synchronization computer determining that the physical model is within a field of view of the augmented reality head mounted display: the AR synchronization computer rendering a virtual image from the virtual model in real time based on the received tracking data; and the AR synchronization computer streaming the virtual image to the augmented reality head mounted display, thereby generating a synchronized and augmented realty view of a physical model.

An example AR synchronization computer includes: first module for receiving synchronization and navigation data from a navigation system, for receiving data representative of a virtual model from a virtual model database, and for receiving tracking data indicative of the position and angle of view of an augmented reality head mounted display with respect to a physical frame of reference; a second module for registering a physical model, for generating a physical frame of reference with respect to the registered physical model based on the synchronization and navigation data, and for registering the augmented reality head mounted display with the navigation system using the synchronization and navigation data, thereby enabling tracking movement of the augmented reality head mounted display with respect to the physical model; a third module for anchoring the virtual model to the physical frame of reference; a fourth module for rendering a virtual image from the virtual model in real time based on the received tracking data responsive to determining that the physical model is within a field of view of the augmented reality head mounted display; and a fifth module for streaming the virtual image to the augmented reality head mounted display, thereby generating a synchronized and augmented realty view of a physical model.

An example system for synchronizing and augmenting a virtual model with a physical model, includes: an augmented reality head mounted display; a virtual model database comprising a virtual three-dimensional model representative of a patient anatomy; a navigation system configured to generate synchronization and navigation data; and an augmented reality synchronization computer comprising one or more processors, one or more computer-readable tangible storage devices, and program instructions stored on at least one of the one or more storage devices for execution by at least one of the one or more processors. The program instructions are configured to: receive synchronization and navigation data from a navigation system and generate a physical frame of reference with respect to a registered physical model based on the synchronization and navigation data; register an augmented reality head mounted display with the navigation system using the synchronization and navigation data, thereby enabling tracking movement of the augmented reality head mounted display with respect to the physical model; receive data representative of a virtual model from a virtual model database; anchor the virtual model to the physical frame of reference; receive tracking data indicative of the position and angle of view of the augmented reality head mounted display with respect to the physical frame of reference; render a virtual image from the virtual model in real time based on the received tracking data responsive to determining that the physical model is within a field of view of the augmented reality head mounted display; and stream the virtual image to the augmented reality head mounted display, thereby generating a synchronized and augmented realty view of a physical model.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

Figure 1:
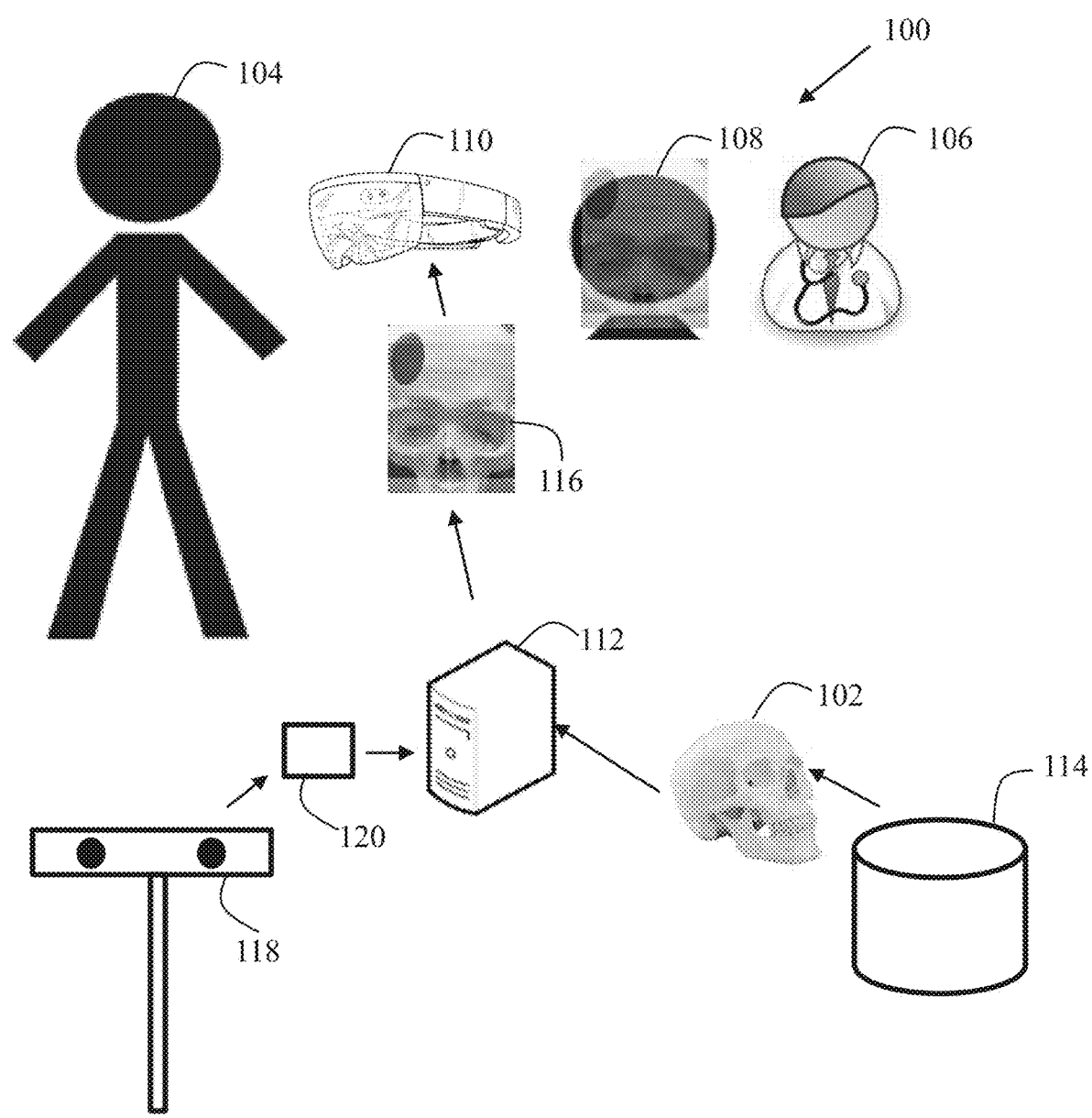
FIG. 1 illustrates an example system for augmenting and synchronizing a virtual model with a physical model.

The following acronyms and definitions will aid in understanding the detailed description:

AR—Augmented Reality—A live view of a physical, real-world environment whose elements have been enhanced by computer generated sensory elements such as sound, video, or graphics.

VR—Virtual Reality—A 3Dimensional computer generated environment which can be explored and interacted with by a person in varying degrees.

HMD—Head Mounted Display refers to a headset which can be used in AR or VR environments. It may be wired or wireless. It may also include one or more add-ons such as headphones, microphone, HD camera, infrared camera, hand trackers, positional trackers etc.

Controller—A device which includes buttons and a direction controller. It may be wired or wireless. Examples of this device are Xbox gamepad, PlayStation gamepad, Oculus touch, etc.

SNAP Model—A SNAP case refers to a 3D texture or 3D objects created using one or more scans of a patient (CT, MR, fMR, DTI, etc.) in DICOM file format. It also includes different presets of segmentation for filtering specific ranges and coloring others in the 3D texture. It may also include 3D objects placed in the scene including 3D shapes to mark specific points or anatomy of interest, 3D Labels, 3D Measurement markers, 3D Arrows for guidance, and 3D surgical tools. Surgical tools and devices have been modeled for education and patient specific rehearsal, particularly for appropriately sizing aneurysm clips.

Avatar—An avatar represents a user inside the virtual environment.

MD6DM—Multi Dimension full spherical virtual reality, 6 Degrees of Freedom Model. It provides a graphical simulation environment which enables the physician to experience, plan, perform, and navigate the intervention in full spherical virtual reality environment.

A surgery rehearsal and preparation tool previously described in U.S. Pat. No. 8,311,791, incorporated in this application by reference, has been developed to convert static CT and MRI medical images into dynamic and interactive multi-dimensional full spherical virtual reality, six (6) degrees of freedom models ("MD6DM") based on a prebuilt SNAP model that can be used by physicians to simulate medical procedures in real time. The MD6DM provides a graphical simulation environment which enables the physician to experience, plan, perform, and navigate the intervention in full spherical virtual reality environment. In particular, the MD6DM gives the surgeon the capability to navigate using a unique multidimensional model, built from traditional two-dimensional patient medical scans, that gives spherical virtual reality 6 degrees of freedom (i.e. linear; x, y, z, and angular, yaw, pitch, roll) in the entire volumetric spherical virtual reality model.

The MD6DM is rendered in real time by an image generator using a SNAP model built from the patient's own data set of medical images including CT, MRI, DTI etc., and is patient specific. A representative brain model, such as Atlas data, can be integrated to create a partially patient specific model if the surgeon so desires. The model gives a 360° spherical view from any point on the MD6DM. Using the MD6DM, the viewer is positioned virtually inside the anatomy and can look and observe both anatomical and pathological structures as if he were standing inside the patient's body. The viewer can look up, down, over the shoulders etc., and will see native structures in relation to each other, exactly as they are found in the patient. Spatial relationships between internal structures are preserved and can be appreciated using the MD6DM.

The algorithm of the MD6DM rendered by the image generator takes the medical image information and builds it into a spherical model, a complete continuous real time model that can be viewed from any angle while "flying" inside the anatomical structure. In particular, after the CT, Mill, etc. takes a real organism and deconstructs it into hundreds of thin slices built from thousands of points, the MD6DM reverts it to a 3D model by representing a 360 view of each of those points from both the inside and outside.

Described herein is an imaging system, leveraging an image generator and a MD6DM model, for creating a synchronized augmented reality view of a subject. In particular, the imaging system enables augmenting and overlaying the MD6DM model over top of a corresponding physical model. A physical model, as used herein, refers to an inanimate physical object that represents a biological system, such as organs, skeletons, body portions (e.g., thorax, brain, nervous system, etc.). For example, a physical model can provide a representation of an actual living person or animal or portion thereof, such as an organ or other part of an anatomy, and might be constructed from actual medical images taken of the person or animal. As another example, physical model can be an inanimate physical representation of an animate object or anatomy, such as a 3-d printed model of a skull or a heart. Although specific references may be made herein to physical models constituting a body or portions of a body, a physical model can also be any physical object, such as a consumer electronic device, a mechanical device, etc. In sum, a physical model may represent any physical representation over which it may be desirable to augment a corresponding virtual model for engaging a patient, for education, for aid in performing a surgical procedure, or for other not medical purposes such as for entertainment, for guidance in performing a task such as a repair, and so on. Furthermore, the techniques discussed herein with respect to the physical model can also be applied to animate objects such as people or animals by substituting the animate object for the physical model, and applying the same approach described for the physical model.

Moreover, the imaging system anchors the MD6DM model to the physical model and synchronizes the two, such that a new image is created and overlayed over top of the physical model according to movement around the model.

This is accomplished by streaming the image generator directly to an HMD, tracking a position and location of the HMD, and adjusting the image generator based on the tracked movement. Thus, a dependency is created between the virtual model and the physical model.

By creating such a dependency and tying or anchoring a virtual model to a physical model, and then adjusting an image overlayed on top of the physical model based on movement with respect to the physical model, a HMD is able to receive a synchronized augmented reality view of the physical model regardless of where a user of the HDM is positioned with respect to the physical model, thus offering the user an improved perspective of the physical model. As a result of anchoring the virtual model to the physical model, the visual model is not separated from the physical model. In other words, if a user of the HMD turns his head and looks away from the physical model, the user will no longer see the virtual model either. Only when the user returns focus to the physical model will the user again see the virtual model, overlayed and synchronized as appropriate. Thus, a user may be presented with the augmented view of a main physical object while still providing the user with the freedom and flexibility to maneuver and interact with secondary physical objects within proximity of the main physical object without interfering with the user's view of or interaction with the secondary objects.

It should be appreciated that although reference is made to anchoring or tying a virtual model to a physical model, the virtual model may be anchored to a physical location, rather than to a physical object, and it is understood that the physical object's position does not move during the augmented reality viewing of the physical object.

It should be appreciated that although the examples described herein may refer in general to medical applications and specifically to virtual models or images of a patient's anatomy augmented and synchronized with a corresponding patient's physical body for the purpose of performing spine surgery, the imaging system may similarly be used to synchronize and augment a virtual model or image of any virtual object with a corresponding physical object.

FIG. 1 illustrates a system 100 for augmenting and synchronizing a virtual model 102 with a physical model 104. In particular, the system 100 enables a user 106, such as a physician, to view an augmented realty view 108 of the physical model 104 from any perspective of the physical model 104. In other words, the user 106 may walk around the physical model 104 and view the physical model 104 from any side, angle, or perspective, and to have the synchronized corresponding view of the virtual model 102 overplayed on top of the physical model 104 in order to form the augmented realty view 108. And, if the user 106 turns away from the physical model 104 such that the physical model 104 is no longer within a current field of view or line of sight, the virtual model 102 similarly is also eliminated from the current view or line of sight.

The system 100 includes an augmented reality head mounted display ("HMD") 110 for providing the user 106 with augmented realty view 108 including a live real life visual of the physical model 104 in combination with additionally integrated content, such as the virtual model 102. For example, the system 100 includes an AR synchronization computer 112 for retrieving a virtual model 102 such as a SNAP model, from a virtual model database 114, for rendering a virtual image 116 from the virtual model 102, and for providing the virtual image 116 to the HMD 110. In one example, the AR synchronization computer 112 includes an image generator (not shown) for rendering the virtual image 116 from the virtual model 102. In another example, the image generator is specific to a virtual model 102 and is included with the virtual model 102 retrieved from the virtual model database 114.

It should be appreciated that although the AR synchronization computer 112 is depicted as being external to the HMD 110, in one example, the AR synchronization computer 112 may be incorporated into the HMD 110. This provides for a single integrated solution for receiving and processing a virtual model 102 so that the HMD 110 may provide the user with the augmented reality view 108 as described. In such an example, the virtual model 102, or image generator for the virtual model 102, is streamed directly to the HMD 110.

The AR synchronization computer 112, in combination with the HMD 110, is configured to tie or anchor the virtual model 102 to the physical model 104 and to synchronize the virtual model 102 with and overlay it on top of the live real life visual of the physical model 104 in order to create the augmented realty view 108 of the physical model 104 via the HMD 110. In order to facilitate anchoring and synchronization, the AR synchronization computer 112 is configured to communicate with a navigation system 118. In particular, the AR synchronization computer 112 is configured to receive synchronization and navigation data 120 from the navigation system 118 and to register the HMD 110 with the navigation system 118 using the received synchronization and navigation data 120. In other words, the synchronization and navigation data 120 from the navigation system 118 serves as a basis for forming a physical frame of reference for the AR synchronization computer 112. This enables the AR synchronization computer 112 to tie the virtual model 102 to the physical model 104 by using the synchronization and navigation data 120, or the navigation system reference frame, as the anchor for the virtual model 102. Once anchored, the AR synchronization computer 112 is able to generate the appropriate virtual image 116 depending on tracked movement of the HMD 110 via the navigation system 118.

Figure 2:
FIG. 2 illustrates an example system for augmenting and synchronizing a virtual model with a physical model.

FIG. 2 illustrates in more detail how the AR synchronization computer 112 interacts with the navigation system 118 in order to synchronize and overlay the virtual model 102 with the physical model 104, as described in FIG. 1. More specifically, a reference array of physical model markers 202 is positioned near a physical model 204 in order to serve as a reference point for registering the physical model 204. By further registering reference points of a probe or surgical tool 206, the navigation system enables tracking of the probe 206 with respect to the physical model 204.

A headset reference array of markers 208 are positioned on a HMD 210 to further enable registration and tracking of the HMD 210 with respect to the physical model 204. Tracking a unicorn-type pointer 212 positioned on the front of the HMD 210 enables more accurate determination of the direction and angle of view of the HMD 210. Thus, the combination of tracking both the probe 206 and the HMD 210 with respect to the reference array of markers 202 positioned near a physical model 204 creates a unique environment within which a virtual model (not shown) may be displayed to a user via the HMD and synchronized with the physical model 204 such as to enable simultaneous interaction with both the virtual model and the physical model 204.

In order to enable a virtual model to be overplayed and properly synchronized with the physical model 204 so that a user may effectively interact with the virtual model in augmented reality, the virtual model is first aligned with the physical model 204. To facilitate alignment, the virtual model includes a virtual representation of the reference array of markers 208 and is positioned virtually, next to the virtual model identical to the position of the reference array of markers 208 with respect to the physical model 204. Initial alignment is then performed by visually lining up the markers of the reference array 208 with the corresponding virtual reference array markers in the virtual model. This can be performed, for example, using an administrative or setup mode of the system prior to engaging or interacting with the models. In one example, the initial alignment or setup may be performed automatically by the AR synchronization computer 112.

Figure 3:
FIG. 3 illustrates an example display of an example system for augmenting and synchronizing a virtual model with a physical model.

Once properly aligned, a user may view the physical model 204 via the HMD 210 while simultaneously and in real time view a synchronized virtual model overlayed on top of the physical model 204 in one integrated augmented view 300, as illustrated in FIG. 3. In one example, the integrated augmented view 300 may also include a virtual probe 302 that is synchronized and overlayed with a physical probe. This enables a user to further interact with the integrated augmented view 300 in manners which may otherwise not be possible with a physical probe alone. For example, as the user moves the physical probe, the corresponding virtual probe 302 may simulate the movements of the physical probe as if it were interacting with the virtual model directly.

Figure 4:
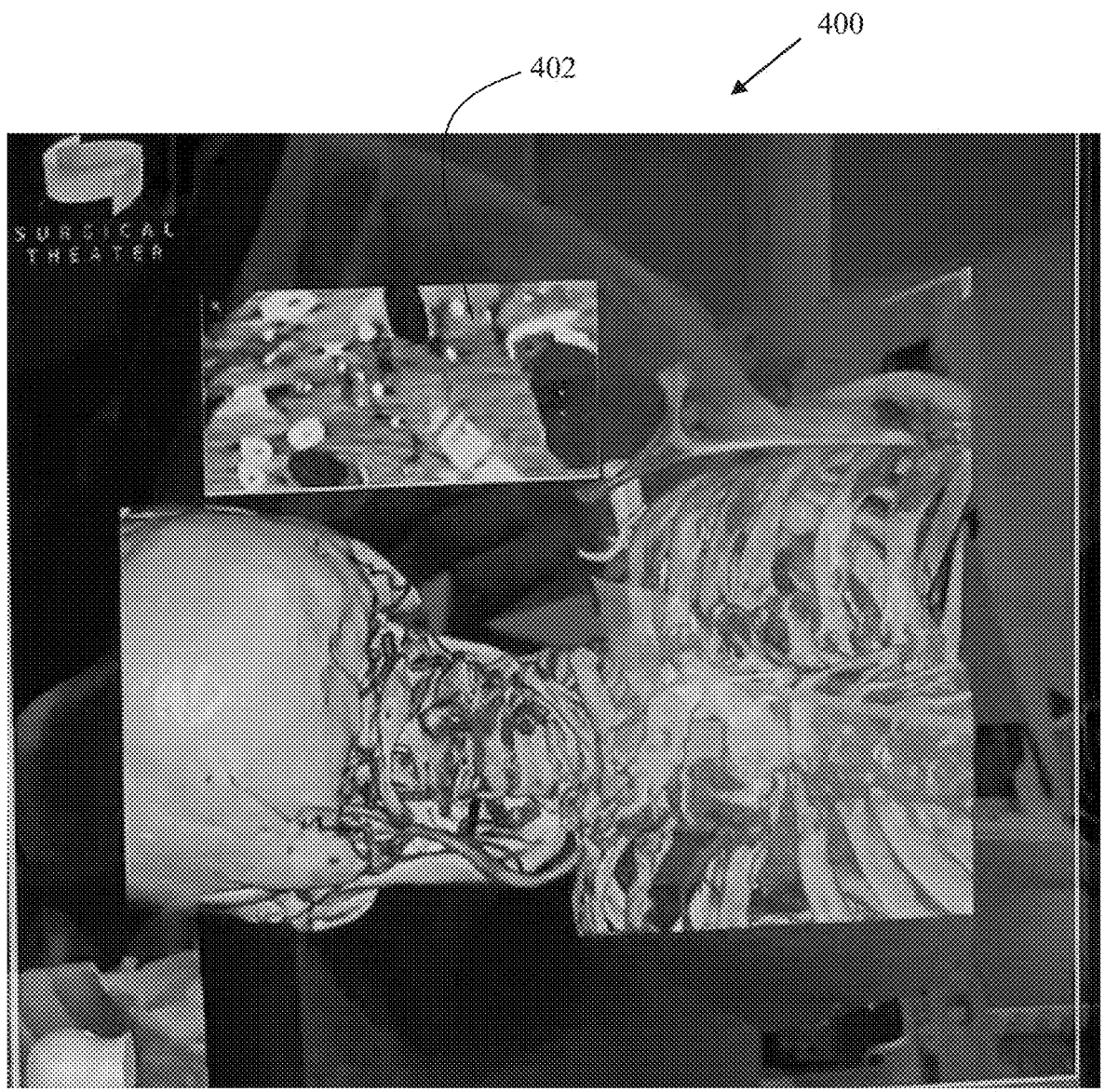
FIG. 4 illustrates an example display of an example system for augmenting and synchronizing a virtual model with a physical model.

In one example, as illustrated in FIG. 4, additional content, such as a DICOM image 402, may be injected into and displayed in an integrated augmented view 400 for the user to further interact with. For example, while viewing and interacting with the integrated augmented view 400, a user may look up or to a side in order to reveal the additional content 402 which may assist the user with the interaction or a surgical procedure, for example.

In one example, a user's interactions and views experienced via a HMD, including both the physical and virtual views as well as any additional injected content, may be live streamed to an external display for additional users to view the same experience.

As can be appreciated, the system described herein provides numerous benefits to a user or a physician. For example, using the augmented reality system for spine surgery, or for any other surgical procedure, allows the surgeon to better prepare for the surgery and perform surgery in a safer manner. This is made possible because of the unique and novel view presented to the surgeon which allows the surgeon to view a combination of bone and anatomy including soft tissue, nerves, spine, blood vessels, lungs, etc. and to view an anatomy even if it is obscured by other tissue.

Figure 5:
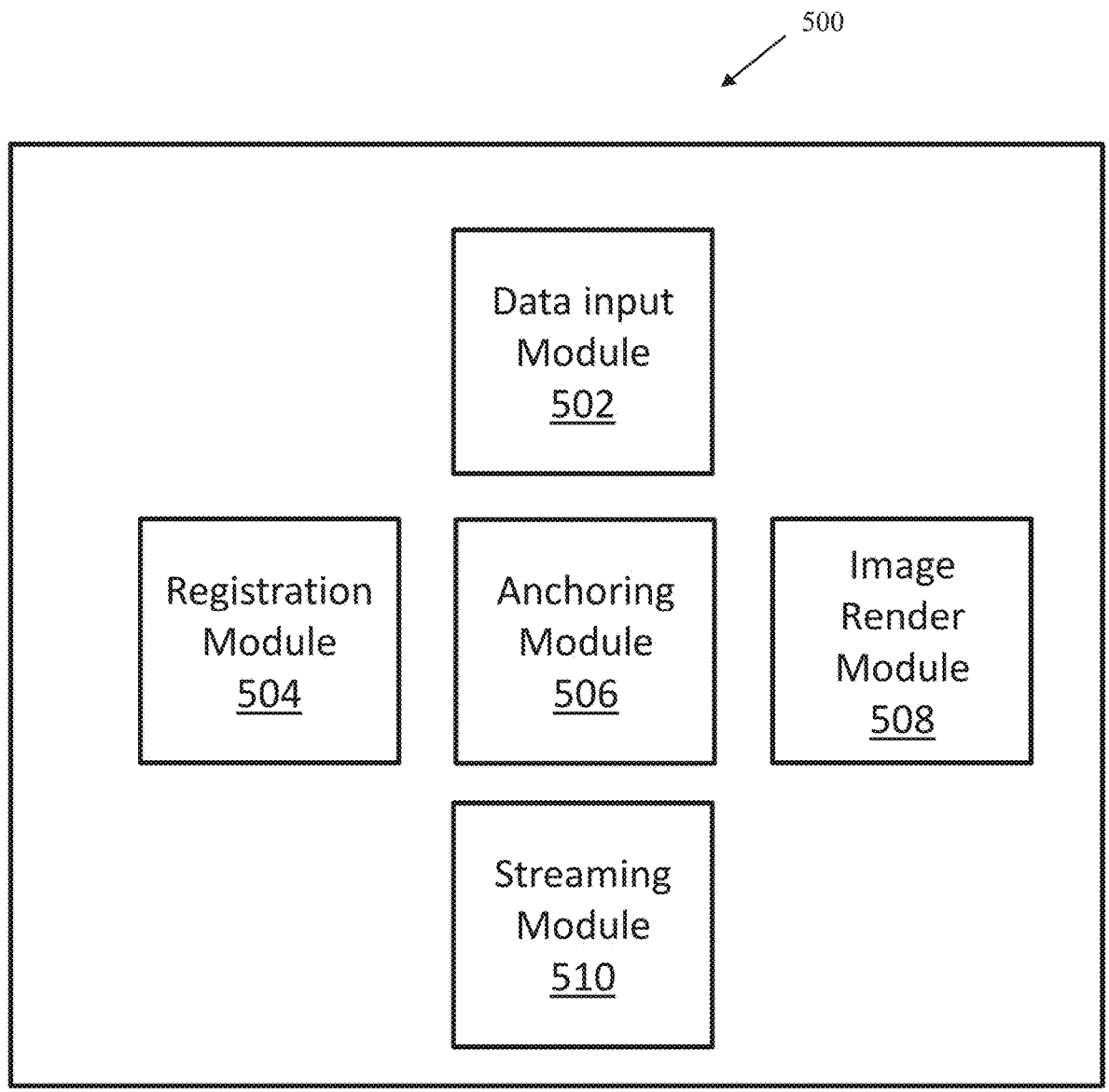
FIG. 5 illustrates an example AR synchronization computer.

FIG. 5 illustrates in more detail an example AR synchronization computer 500 such as the AR synchronization computer 112 of FIG. 1. The AR synchronization computer 500 incudes a data input module 502 for receiving synchronization and navigation data from a navigation system. The data input module 502 further receives data representative of a virtual model from a virtual model database. The data input module 502 further receives tracking data indicative of the position and angle of view of the augmented reality head mounted display with respect to the physical frame of reference. The AR synchronization computer 500 further includes a registration module 504 for registering a physical model and for generating a physical frame of reference with respect to the registered physical model based on the synchronization and navigation data. The registration module 504 further registers an augmented reality head mounted display with the navigation system using the synchronization and navigation data, thereby enabling tracking movement of the augmented reality head mounted display with respect to the physical model. The AR synchronization computer 500 further includes an anchoring module 506 for anchoring the virtual model to the physical frame of reference. The AR synchronization computer 500 further includes an image render module 508 for rendering a virtual image from the virtual model in real time based on the received tracking data. The AR synchronization computer 500 further includes a streaming module 510 for streaming the virtual image to the augmented reality head mounted display, thereby generating a synchronized and augmented realty view of a physical model.

Figure 6:
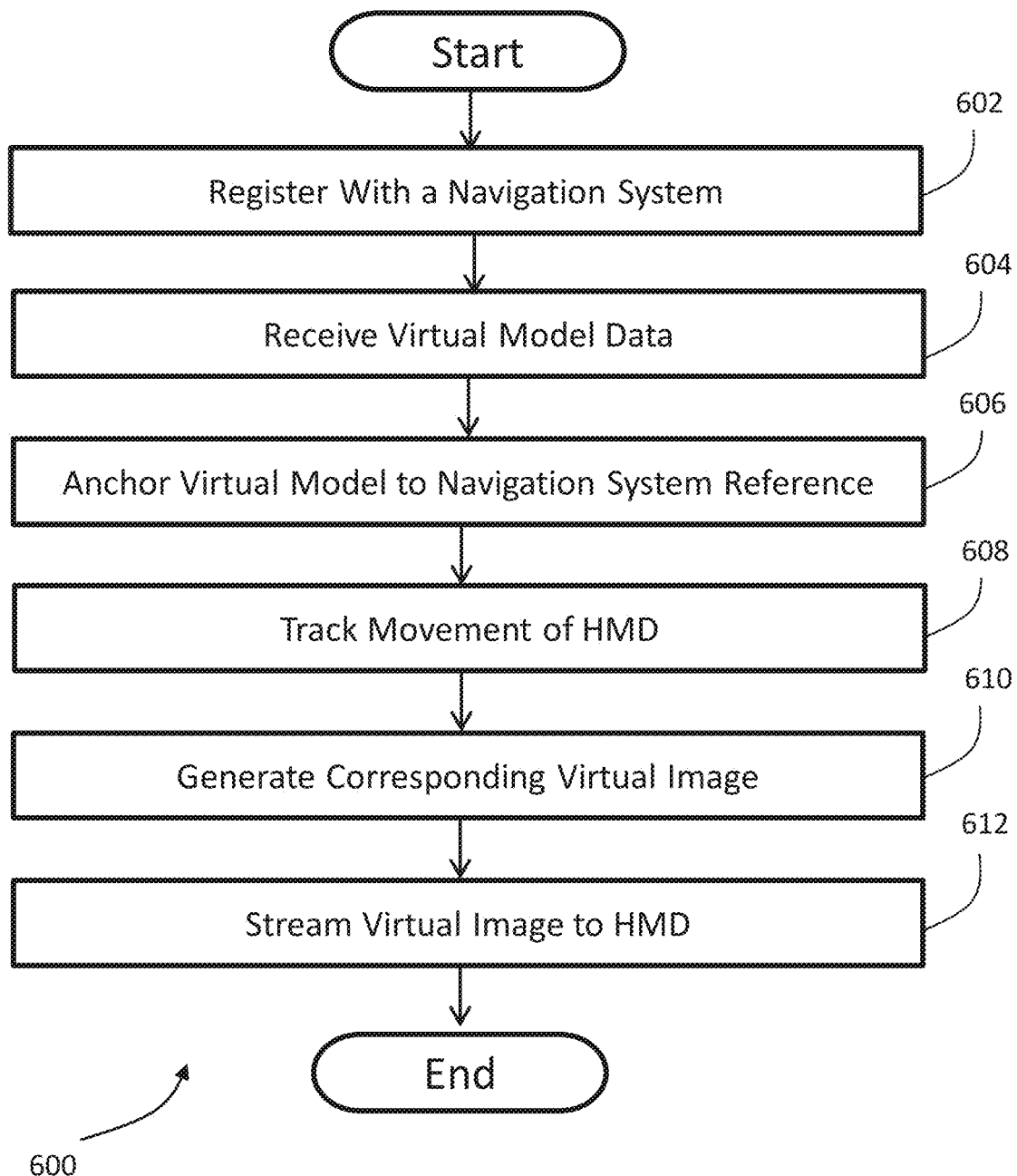
FIG. 6 illustrates an example method for augmenting and synchronizing a virtual model with a physical model.

FIG. 6 illustrates an example method for synchronizing and augmenting a virtual model with a physical model. At 602, the AR synchronization computer 112 receives synchronization and navigation data 120 from the navigation system 118 and registers the HMD 110 with the navigation system 118. At 604, the AR synchronization computer 112 receives data representative of a virtual model 102 from the virtual model database 114. At 606, the AR synchronization computer 112 anchors the virtual model 102 to the navigation system 118 reference. At 608, the AR synchronization computer 112 receives tracking data indicative of movement of the HMD 110. In one example, the tracking data is received from the navigation system 118. In another example, the tracking data is received from the HMD 110. At 610, the AR synchronization computer 112 renders the virtual image 116 from the virtual model 102 based on the received tracking data. At 612, the AR synchronization computer 112 streams the virtual image 116 to the HMD 110 in order to generate the augmented realty view 108 of the physical model 104.

Figure 7:
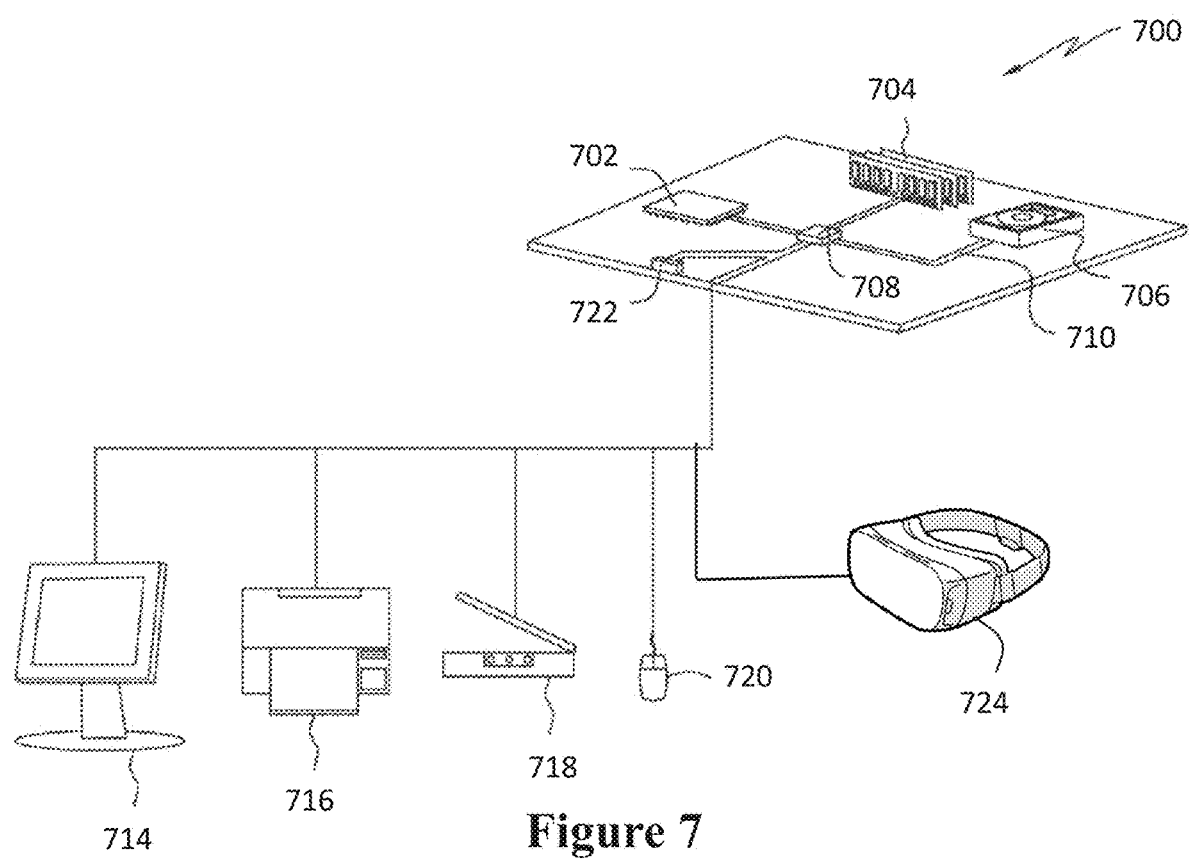
FIG. 7 illustrates an example computer implementing the example augmented reality synchronization computer of FIG. 1.

FIG. 7 is a schematic diagram of an example computer for implementing the AR synchronization computer 112 of FIG. 1. The example computer 700 is intended to represent various forms of digital computers, including laptops, desktops, handheld computers, tablet computers, smartphones, servers, and other similar types of computing devices. Computer 700 includes a processor 702, memory 704, a storage device 706, and a communication port 708, operably connected by an interface 710 via a bus 712.

Processor 702 processes instructions, via memory 704, for execution within computer 600. In an example embodiment, multiple processors along with multiple memories may be used.

Memory 704 may be volatile memory or non-volatile memory. Memory 704 may be a computer-readable medium, such as a magnetic disk or optical disk. Storage device 706 may be a computer-readable medium, such as floppy disk devices, a hard disk device, optical disk device, a tape device, a flash memory, phase change memory, or other similar solid state memory device, or an array of devices, including devices in a storage area network of other configurations. A computer program product can be tangibly embodied in a computer readable medium such as memory 704 or storage device 706.

Computer 700 can be coupled to one or more input and output devices such as a display 714, a printer 716, a scanner 718, a mouse 720, and a HMD 724.

As will be appreciated by one of skill in the art, the example embodiments may be actualized as, or may generally utilize, a method, system, computer program product, or a combination of the foregoing. Accordingly, any of the embodiments may take the form of specialized software comprising executable instructions stored in a storage device for execution on computer hardware, where the software can be stored on a computer-usable storage medium having computer-usable program code embodied in the medium.

Databases may be implemented using commercially available computer applications, such as open source solutions such as MySQL, or closed solutions like Microsoft SQL that may operate on the disclosed servers or on additional computer servers. Databases may utilize relational or object oriented paradigms for storing data, models, and model parameters that are used for the example embodiments disclosed above. Such databases may be customized using known database programming techniques for specialized applicability as disclosed herein.

Any suitable computer usable (computer readable) medium may be utilized for storing the software comprising the executable instructions. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet.

In the context of this document, a computer usable or computer readable medium may be any medium that can contain, store, communicate, propagate, or transport the program instructions for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, local communication busses, radio frequency (RF) or other means.

Computer program code having executable instructions for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, C#, Object Pascal, or the like, artificial intelligence languages such as Prolog, a real-time embedded language such as Ada, or even more direct or simplified programming using ladder logic, an Assembler language, or directly programming using an appropriate machine language.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

The invention claimed is:

1. A method for synchronizing and augmenting a virtual model with a physical model, comprising the steps of:

an AR synchronization computer receiving synchronization and navigation data from a navigation system and generating a physical frame of reference with respect to a registered physical model based on the synchronization and navigation data;

the AR synchronization computer registering an augmented reality head mounted display with the navigation system using the synchronization and navigation data, thereby enabling tracking movement of the augmented reality head mounted display with respect to the physical model;

the AR synchronization computer receiving data representative of a virtual model from a virtual model database;

the AR synchronization computer anchoring the virtual model to the physical frame of reference;

the AR synchronization computer receiving tracking data indicative of a position and angle of view of the augmented reality head mounted display with respect to the physical frame of reference; and responsive to the AR synchronization computer determining that the physical model is within a field of view of the augmented reality head mounted display;

the AR synchronization computer rendering a virtual image from the virtual model in real time based on the received tracking data;

the AR synchronization computer streaming the virtual image to the augmented reality head mounted display, thereby generating a synchronized and augmented reality view of the physical model;

the AR synchronization computer registering a physical surgical tool having a plurality of markers with the navigation system using the synchronization and navigation data, thereby enabling tracking movement of the physical surgical tool with respect to the physical model;

the AR synchronization computer generating a virtual surgical tool representative of the physical surgical tool and comprising a plurality of virtual representations of the surgical tool markers;

the AR synchronization computer aligning the virtual surgical tool with the physical surgical tool by aligning the virtual representations of the physical tool markers with the physical tool markers; and the AR synchronization computer streaming the virtual image to the augmented reality head mounted display further comprises streaming the virtual surgical tool to the augmented reality head mounted display.

2. The method of claim 1, wherein the step of the AR synchronization computer rendering a virtual image from the virtual model and streaming the virtual image to the augmented reality head mounted display comprises the AR synchronization computer streaming to the augmented reality head mounted display an image generator configured to render a virtual image from the virtual model.

3. The method of claim 1, wherein the AR synchronization computer registers the physical model using a plurality of physical model markers disposed proximate to the physical model, and wherein the AR synchronization computer registers the augmented reality head mounted display using a plurality of head mounted display markers disposed on the augmented reality head mounted display.

4. The method of claim 3, further comprising the step of aligning the virtual model with the physical model, wherein the virtual model comprises a plurality of virtual representations of the physical model markers, and wherein the aligning the virtual model with the physical model comprises aligning the virtual representations of the physical model markers with the physical model markers.

5. The method of claim 1, wherein the AR synchronization computer streaming the virtual image to the augmented reality head mounted display further comprises streaming a DICOM image and injecting the DICOM image into the synchronized and augmented reality view of a physical model.

6. The method of claim 5, further comprising the AR synchronization computer live streaming to an external display a user's interactions and views experienced via the head mounted display, including the physical model, the virtual model, and the DICOM image.

7. An AR synchronization computer comprising:
a first module for receiving synchronization and navigation data from a navigation system, for receiving data representative of a virtual model from a virtual model database, and for receiving tracking data indicative of a position and angle of view of an augmented reality head mounted display with respect to a physical frame of reference;
a second module for registering a physical model, for generating a physical frame of reference with respect to the registered physical model based on the synchronization and navigation data, and for registering the augmented reality head mounted display with the navigation system using the synchronization and navigation data, thereby enabling tracking movement of the augmented reality head mounted display with respect to the physical model;
a third module for anchoring the virtual model to the physical frame of reference;
a fourth module for rendering a virtual image from the virtual model in real time based on the received tracking data responsive to determining that the physical model is within a field of view of the augmented reality head mounted display; and
a fifth module for streaming the virtual image to the augmented reality head mounted display, thereby generating a synchronized and augmented reality view of the physical model, wherein the AR synchronization computer generates a virtual surgical tool representative of the physical surgical tool and comprising a plurality of virtual representations of the surgical tool markers, and wherein:
the second module is configured to register a physical surgical tool having a plurality of markers with the navigation system using the synchronization and navigation data, thereby enabling tracking movement of the physical surgical tool with respect to the physical model, and aligning the virtual surgical tool with the physical surgical tool by aligning the virtual representations of the physical tool markers with the physical tool markers, and wherein
the fifth module is further configured to stream the virtual surgical tool to the augmented reality head mounted display.

8. The AR synchronization computer of claim 7, wherein the fourth module comprises an image generator for rendering virtual image, and wherein the fifth module is configured to stream the image generator to the augmented reality head mounted display.

9. The AR synchronization computer of claim 7, wherein the second module is configured to register the physical model using a plurality of physical model markers disposed proximate to the physical model, and configured to register the augmented reality head mounted display using a plurality of head mounted display markers disposed on the augmented reality head mounted display.

10. The AR synchronization computer of claim 9, wherein the virtual model comprises a plurality of virtual representations of the physical model markers, and wherein the third module is configured to align the virtual model with the physical model by aligning the virtual representations of the physical model markers with the physical model markers.

11. The AR synchronization computer of claim 7, wherein the fifth module is further configured to stream a DICOM image and inject the DICOM image into the synchronized and augmented reality view of a physical model.

12. The AR synchronization computer of claim 11, wherein the fifth module is further configured to live stream to an external display a user's interactions and views experienced via the head mounted display, including the physical model, the virtual model, and the DICOM image.

13. A system for synchronizing and augmenting a virtual model with a physical model, the system comprising:
an augmented reality head mounted display;
a virtual model database comprising a virtual three-dimensional model representative of a patient anatomy;
a navigation system configured to generate synchronization and navigation data; and
an augmented reality synchronization computer comprising one or more processors, one or more computer-readable tangible storage devices, and program instructions stored on at least one of the one or more storage devices for execution by at least one of the one or more processors, the program instructions configured to:
receive synchronization and navigation data from a navigation system and generate a physical frame of reference with respect to a registered physical model based on the synchronization and navigation data;
register an augmented reality head mounted display with the navigation system using the synchronization and navigation data, thereby enabling tracking movement of the augmented reality head mounted display with respect to the physical model;
receive data representative of a virtual model from a virtual model database;

anchor the virtual model to the physical frame of reference;

receive tracking data indicative of a position and angle of view of the augmented reality head mounted display with respect to the physical frame of reference;

render a virtual image from the virtual model in real time based on the received tracking data responsive to determining that the physical model is within a field of view of the augmented reality head mounted display; and stream the virtual image to the augmented reality head mounted display, thereby generating a synchronized and augmented reality view of the physical model, wherein the program instructions are further configured to:
   register a physical surgical tool having a plurality of markers with the navigation system using the synchronization and navigation data, thereby enabling tracking movement of the physical surgical tool with respect to the physical model,
   generate a virtual surgical tool representative of the physical surgical tool and comprising a plurality of virtual representations of the surgical tool markers,
   align the virtual surgical tool with the physical surgical tool by aligning the virtual representations of the physical tool markers with the physical tool markers, and
   stream the virtual surgical tool to the augmented reality head mounted display.

14. The system of claim 13, wherein the program instructions are further configured to stream to the augmented reality head mounted display an image generator configured to render a virtual image from the virtual model.

15. The system of claim 13, wherein the program instructions are further configured to register the physical model using a plurality of physical model markers disposed proximate to the physical model, and to register the augmented reality head mounted display using a plurality of head mounted display markers disposed on the augmented reality head mounted display.

16. The system of claim 15, wherein the virtual model comprises a plurality of virtual representations of the physical model markers, and wherein the program instructions are further configured to align the virtual model with the physical model by aligning the virtual representations of the physical model markers with the physical model markers.

17. The system of claim 13, wherein the program instructions are further configured to stream a DICOM image and inject the DICOM image into the synchronized and augmented reality view of the physical model.

* * * * *